United States Patent
Rademacher et al.

(10) Patent No.: US 8,044,084 B2
(45) Date of Patent: Oct. 25, 2011

(54) MIXTURE COMPRISING STROBILURINS AND ETHYLENE MODULATORS

(75) Inventors: Wilhelm Rademacher, Limburgerhof (DE); John S. Harden, Raleigh, NC (US); Dan E. Westberg, Cary, NC (US); Joseph E. Zawierucha, Cary, NC (US); Thomas J. Holt, Holly Springs, NC (US); Hendrik Ypema, Research Triangle, NC (US); Ted R. Bardinelli, Durham, NC (US); Albert C. Everson, Cary, NC (US); Edson Begliomini, Sao Paulo (BR)

(73) Assignee: BASF SE, Ludwigshafen (DE)

( * ) Notice: Subject to any disclaimer, the term of this patent is extended or adjusted under 35 U.S.C. 154(b) by 1063 days.

(21) Appl. No.: 10/578,333

(22) PCT Filed: Nov. 5, 2004

(86) PCT No.: PCT/EP2004/012514
§ 371 (c)(1),
(2), (4) Date: May 4, 2006

(87) PCT Pub. No.: WO2005/044002
PCT Pub. Date: May 19, 2005

(65) Prior Publication Data
US 2007/0093389 A1    Apr. 26, 2007

Related U.S. Application Data

(60) Provisional application No. 60/517,883, filed on Nov. 7, 2003.

(51) Int. Cl.
| | |
|---|---|
| A01N 43/56 | (2006.01) |
| A01N 37/00 | (2006.01) |
| A01N 35/00 | (2006.01) |
| A01N 59/16 | (2006.01) |
| A01N 63/00 | (2006.01) |
| A01N 59/06 | (2006.01) |
| A01N 43/58 | (2006.01) |
| A01N 43/64 | (2006.01) |
| A01N 43/50 | (2006.01) |
| A01N 55/00 | (2006.01) |
| A01N 43/54 | (2006.01) |

(52) U.S. Cl. ........ 514/407; 514/557; 514/690; 514/383; 514/399; 514/63; 514/266.23; 514/384; 424/646; 504/118; 504/121; 504/238; 504/320

(58) Field of Classification Search .......... 514/407, 514/557
See application file for complete search history.

(56) References Cited

U.S. PATENT DOCUMENTS

| | | |
|---|---|---|
| 4,560,403 A | 12/1985 | Motojima et al. |
| 4,678,496 A | 7/1987 | Motojima et al. |
| 4,744,811 A | 5/1988 | Schulz et al. |
| 4,866,201 A | 9/1989 | Motojima et al. |
| 5,364,834 A | 11/1994 | Kirchner et al. |
| 5,869,424 A | 2/1999 | Rademacher et al. |
| 6,180,638 B1 | 1/2001 | Muller et al. |
| 6,245,792 B1 | 6/2001 | Muller et al. |
| 6,344,469 B1 | 2/2002 | Schelberger et al. |
| 6,369,003 B1 | 4/2002 | Rademacher et al. |
| 6,369,090 B1 | 4/2002 | Schelberger et al. |
| 2003/0060371 A1 | 3/2003 | Asrar et al. |

FOREIGN PATENT DOCUMENTS

| | | |
|---|---|---|
| EP | 0 123 001 B1 | 4/1990 |
| EP | 0 243 834 B1 | 5/1991 |
| EP | 0 501 326 B1 | 10/1995 |
| EP | 0 767 607 B1 | 11/1998 |
| JP | 2002-173402 A | 6/2002 |
| WO | WO-96/00005 A1 | 1/1996 |
| WO | WO-97/40688 A1 | 11/1997 |
| WO | WO-99/48370 A1 | 9/1999 |
| WO | WO-02/068367 A1 | 9/2002 |

OTHER PUBLICATIONS

Dave W Bartlett, John M Clough, Jeremy R Godwin, Alison A Hall, Mick Hamer and Bob Parr-Dobrzanski, "The strobilurin fungicides", Pest Management Science, 2002, 58, 649-662.*
M. Lodovica Gullino, Pierre Leroux, Constance M. Smith, "Uses and challenges of novel compounds for plant disease control", Crop Protection, 2000, 19, 1-11.* Y. Elad, "Regulators of ethylene biosynthesis or activity as a tool for reducing susceptibility of host plant tissues to infection by Botrytis cinerea", The Netherlands Journal of Plant Pathology, 1993, 99, 105-113.*
Scorr Grover and William K. Purves, "Cobalt and Plant Development", Plant Physiology, 1976, 57, 886-889.*
Sisler E. C. et al., "Compounds Interacting with the Ethylene Receptor in Plants.", Plant Biology, vol. 5, No. 5, pp. 473-480, 2003.
Beyer E. M., Jr., "A Potent Inhibitor of Ethylene Action in Plants", Plant Physiology, vol. 58, No. 3, pp. 268-271, 1976.

(Continued)

Primary Examiner — John Pak
Assistant Examiner — Nathan W Schlientz
(74) Attorney, Agent, or Firm — Brinks Hofer Gilson & Lione

(57) ABSTRACT

The present invention relates to mixtures comprising
a) a compound of the formula I

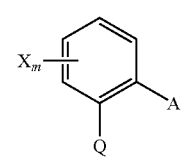

in which X, m, Q and a are as defined in the description and
b) one or more ethylene modulators (II) selected from the group consisting of:
   inhibitors of ethylene biosynthesis which inhibit the conversion of S-adenosyl-L-methionine into 1-aminocyclopropane-1-carboxylic acid (ACC),
   inhibitors of ethylene biosynthesis which block the conversion of ACC into ethylene, or
   inhibitors of ethylene action, and also
to compositions comprising them and to their use for controlling harmful fungi.

10 Claims, No Drawings

OTHER PUBLICATIONS

Altman Steven A. et al., "Inhibition of ethylene biosynthesis and action in cut carnations (*Dianthus caryophyllus* L.) by aminotriazole", Database Biosis, Biosciences Information Service, Philadelphia, PA, US, Journal of the American Society for Horticultural Science, vol. 119, No. 2, pp. 282-287, 1994, Database accession No. PREV199497223765, (XP002503115).

Lieberman, Ann. Rev. Plant Physiol., vol. 30, pp. 533-591(1979).

Yang et al., Ann. Rev. Plant Physiol, vol. 35, pp. 155-189, (1984).

Sisler et al., Plant Growth Regulation, vol. 40, pp. 223-228, (2003).

Kirchner et al., Plant Growth Regulation, vol. 13, pp. 41-46, (1993).

Leslie et al., Plant Physiol., vol. 88, pp. 833-837, (1988).

Grossman et al., Pestic. Sci., vol. 50, pp. 11-20, (1997).

Kohle et al., Gesunde Pflanzen, vol. 49, Section 8, pp. 267-271, (1997).

Rademacher., Annu. Rev., Plant Physiol, Plant Mol. Biol., vol. 51, pp. 501-351, (2000).

Bazzi et al., Europ.J.Hort.Sci., vol. 68, Section (3).S., pp. 108-114 (2003). ISSN 1611-4426.

Tomlin, The e-Pesticide Manuel, 13th Ed., Version 3.0, (Nov. 2003).

Jabs et al., The BCPC Conference—Pests & Diseases, vol. 2, pp. 941-946, (2002).

\* cited by examiner

MIXTURE COMPRISING STROBILURINS AND ETHYLENE MODULATORS

This application is the national phase of PCT application PCT/EP2004/012514 filed on Nov. 5, 2004 which claims priority under 35 U.S.C. 119(e) on U.S. Provisional Application No(s). 60/517,883 filed on Nov. 7, 2003. The entire contents of the above documents is hereby incorporated by reference.

The invention relates to mixtures comprising
a) a compound of the formula I

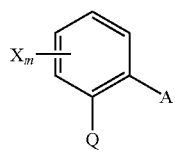

in which
X is halogen, $C_1$-$C_4$-alkyl or trifluormethyl;
m is 0 or 1;
Q is $C(=CH-CH_3)-COOCH_3$, $C(=CH-OCH_3)-COOCH_3$, $C(=N-OCH_3)-CONHCH_3$, $C(=N-OCH_3)-COOCH_3$ or $N(-OCH_3)-COOCH_3$;
A is $-O-B$, $-CH_2O-B$, $-OCH_2-B$, $-CH=CH-B$, $-C\equiv C-B$, $-CH_2O-N=C(R^1)-B$ or $-CH_2O-N=C(R^1)-C(R^2)=N-OR^3$, where
  B is phenyl, naphthyl, 5-membered or 6-membered hetaryl or 5-membered or 6-membered heterocyclyl which contains one to three nitrogen atoms and/or one oxygen or sulfur atom or one or two oxygen and/or sulfur atoms, where the ring systems are unsubstituted or substituted by one to three radicals $R^a$:
    $R^a$ is cyano, nitro, amino, aminocarbonyl, aminothiocarbonyl, halogen, $C_1$-$C_6$-alkyl, $C_1$-$C_6$-haloalkyl, $C_1$-$C_6$-alkylcarbonyl, $C_1$-$C_6$-alkylsulfonyl, $C_1$-$C_6$-alkylsulfoxyl, $C_3$-$C_6$-cycloalkyl, $C_1$-$C_6$-alkoxy, $C_1$-$C_6$-haloalkoxy, $C_1$-$C_6$-alkyloxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, phenyl, phenoxy, benzyl, benzyloxy, 5- or 6-membered heterocyclyl, 5- or 6-membered hetaryl, 5- or 6-membered hetaryloxy, $C(=NOR')-OR''$ or $OC(R')_2-C(R'')=NOR''$,
    where the cyclic radicals for their part are unsubstituted or substituted by one to three radicals $R^b$:
    $R^b$ is cyano, nitro, halogen, amino, aminocarbonyl, aminothiocarbonyl, $C_1$-$C_6$-alkyl, $C_1$-$C_6$-haloalkyl, $C_1$-$C_6$-alkylsulfonyl, $C_1$-$C_6$-alkylsulfoxyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, $C_3$-$C_6$-cycloalkyl, $C_3$-$C_6$-cycloalkenyl, phenyl, phenoxy, phenylthio, benzyl, benzyloxy, 5- or 6-membered heterocyclyl, 5- or 6-membered hetaryl, 5- or 6-membered hetaryloxy or $C(=NOR')-OR''$;
    $R'$ is hydrogen, cyano, $C_1$-$C_6$-alkyl, $C_3$-$C_6$-cycloalkyl or $C_1$-$C_4$-haloalkyl;
    $R^*$ is hydrogen, $C_1$-$C_6$-alkyl, $C_3$-$C_6$-alkenyl, $C_3$-$C_6$-alkinyl, $C_1$-$C_4$-haloalkyl, $C_3$-$C_6$-haloalkenyl or $C_3$-$C_6$-haloalkinyl;
  $R^1$ is hydrogen, cyano, $C_1$-$C_4$-alkyl, $C_1$-$C_4$-haloalkyl, $C_3$-$C_6$-cycloalkyl, $C_1$-$C_4$-alkoxy;
  $R^2$ is phenyl, phenylcarbonyl, phenylsulfonyl, 5- or 6-membered hetaryl, 5- or 6-membered hetarylcarbonyl or 5- or 6-membered hetarylsulfonyl, where the ring systems are unsubstituted or substituted by one to three radicals $R^a$,
    is $C_1$-$C_{10}$-alkyl, $C_3$-$C_6$-cycloalkyl, $C_2$-$C_{10}$-alkenyl, $C_2$-$C_{10}$-alkinyl, $C_1$-$C_{10}$-alkylcarbonyl, $C_2$-$C_{10}$-alkenylcarbonyl, $C_3$-$C_{10}$-alkinylcarbonyl, $C_1$-$C_{10}$-alkylsulfonyl or $C(R')=NOR''$, where the hydrocarbon radicals of these groups are unsubstituted or substituted by one to three radicals $R^c$:
    $R^c$ is cyano, nitro, amino, aminocarbonyl, aminothiocarbonyl, halogen, $C_1$-$C_6$-alkyl, $C_1$-$C_6$-haloalkyl, $C_1$-$C_6$-alkylsulfonyl, $C_1$-$C_6$-alkylsulfoxyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, $C_3$-$C_6$-cycloalkyl, $C_3$-$C_6$-cycloalkyloxy, 5- or 6-membered heterocyclyl, 5- or 6-membered heterocyclyloxy, benzyl, benzyloxy, phenyl, phenoxy, phenylthio, 5- or 6-membered hetaryl, 5- or 6-membered hetaryloxy or hetarylthio, where the cyclic groups for their part may be partially of fully halogenated or may carry one to three radicals $R^a$; and
  $R^3$ is hydrogen, $C_1$-$C_6$-alkyl, $C_2$-$C_6$-alkenyl or $C_2$-$C_6$-alkinyl where the hydrocarbon radicals of these groups may be unsubstituted or substituted by one to three radicals $R^c$;
and
b) one or more ethylene modulators (II) selected from the group consisting of:
  ethylene biosynthesis inhibitors which inhibit the conversion of S-adenosyl-L-methionine into 1-aminocyclopropane-1-carboxylic acid (ACC), such as derivatives of vinylglycine, hydroxylamines, oxime ether derivatives;
  ethylene biosynthesis inhibitors which block the conversion of ACC into ethylene, selected from the group consisting of: $Co^{++}$ or $Ni^{++}$ ions in plant-available forms; phenolic radical scavengers such as n-propyl gallate; polyamines, such as putrescine, spermine or spermidine; structural analogs of ACC, such as α-aminoisobutyric acid or L-aminocyclopropene-1-carboxylic acid; salicylic acid or acibenzolar-S-methyl; structural analogs of ascorbic acid which act as inhibitors of ACC oxidase, such as prohexadione-Ca or trinexapac-ethyl; and triazolyl compounds such as paclobutrazol or uniconazole as inhibitors of cytochrome P-450-dependent monooxygenases, whose main action is to block the biosynthesis of gibberellins;
  inhibitors of the action of ethylene selected from the group consisting of: structural analogs of ethylene such as 1-methylcyclopropene or 2,5-norbornadiene and 3-amino-1,2,4-triazole or Ag$^{++}$ ions in a weight ratio of I to II of from 20:1 to 0.05:1.

Furthermore, the invention relates to a method for controlling harmful fungi such as *Phakopsora pachyrhizi* or *Phakopsora meibomiae* on legumes and to a method for increasing the yield of legumes by using the mixtures according to the invention.

Also the present invention relates to a method for reducing the ethylene evolution of plants and to a method for reducing undesired defoliation of crop plants.

Until recently, in the most important regions of cultivation of legumes (in particular soybeans) there were no infections by harmful fungi such as rust which were of major economical importance. In 2001 and 2002, however, there were increasing incidents of strong rust infections in South America by the harmful fungi *Phakopsora pachyrhizi* and *Phakopsora meibomiae* in crops of soybeans. There were considerable harvest and yield losses. In addition to soybeans, these harmful fungi also attack other legume genera and species.

In the literature, compounds of the formula I are known under the name strobilurins. Like the azoles (III), they belong to the modern and highly effective fungicidally active compounds (see, for example, Angew. Chem. Int. Ed. 1999, 38, 1328-1349; Pesticide Manual, editor C. Tomlin, 12$^{th}$ edition). Hitherto, little has been known concerning the action of the abovementioned compounds specifically against harmful fungi such as *Phakopsora pachyrhizi* and *Phakopsora meibomiae*.

In the specialist literature few results were found, for example:

http://www.saspp.org/archived_articles/tablesoybean-rust_2002.html Cyproconazole, tridimend, flusilazole, tebuconazole, flusilazole+carbentazim, difenoconazole tridimend and triforine have been used as emergency fungicides for soybean rust control in South Africa for the growing season 2001/2002.

http://www.aphis.usda.gov/ppq/ep/soybean_rust/UreMelPp502.pdf In Zimbabwe following fungicides have been approved for the control of soybean rust: cyproconazole, tebuconazole, triforine, flutriafol, flusilazole+carbentazim, difenoconazole, triadimenol and propiconazole.

However, recent documents teach the use of stobilurin fungicides to control soybean rust, like:

http://www.ipmcenters.org/NewsAlerts/soybeanrust/Brazil2002.pdf In Brazil tests have been conducted with Topsin 500 SC (thiophanate), Stratego 250 EC (trifloxystrobin+propiconazole), tebuconazole and tebuconazole+triadimenol for the control of soybean rust in 2002.

http://www.ipmcenters.org/NewsAlerts/soybeanrust/USDA.pdf Also in Paraguay trials have been conducted with various fungicides like azoxystrobin, propiconazole, fenbuconazole, mancozep etc. to evaluate soybean rust control there.

All fungicide recommendations given here appear to have a rather preliminary character. Effects on leaf drop are not described.

A further problem consists in the fact that even by using extremely effective fungicides, it is not possible completely to avoid damage to the plants. Following infection, the assimilation performance of the plants is reduced by leaf necroses occurring. Furthermore, in the soybean plant, the pathogens cause premature aging of the leaves and defoliation of the plants. This results in harvest and yield losses. It was an object of the present invention to provide a method which allows both control of the harmful fungi and the premature leaf drop caused by the harmful fungi in the host plants to be prevented.

We have found that this object is achieved, surprisingly, by applying the combination according to the invention of a strobilurin fungicide and an ethylene modulator. Following the control of harmful fungi with the mixture according to the invention, the host plants are damaged to a considerably lesser degree than after treatment with a customary fungicide.

Ethylene modulators are to be understood as meaning substances which block the natural formation of the plant hormone ethylene or else its action. [Reviews for example in M. Lieberman (1979), Biosynthesis and action of ethylene, Annual Review of Plant Physiology 30: 533-591//S. F. Yang and N. E. Hoffman (1984), Ethylene biosynthesis and its regulation in higher plants, Annual Review of Plant Physiology 35: 155-189//E. S. Sisler et. al. (2003), 1-substituted cyclopropenes: Effective blocking agents for ethylene action in plants, Plant Growth Regulation 40: 223-228]. Essentially, three groups have to be distinguished here:

Inhibitors of ethylene biosynthesis which inhibit the conversion of S-adenosyl-L-methionine into 1-aminocyclopropane-1-carboxylic acid (ACC) for example vinylglycine derivatives (rhizobitoxin, aminoethoxyvinylglycine, methoxyvinylglycine), hydroxylamines (L-canaline, aminooxyacetic acid) or oxime ether derivatives [according to EP-A-0 243 834 and EP-A 0 501 326 or J. Kirchner et al. (1993), Effects of novel oxime ether derivatives of aminoon/acetic acid on ethylene formation in leaves of oilseed rape and barley and on carnation flower senescence, Plant Growth Regulation 13: 41-46].

Inhibitors of ethylene biosynthesis which block the conversion of ACC into ethylene for example Co$^{++}$ or Ni$^{++}$ ions, radical-scavenging phenolic substances (for example n-propyl gallate), polyamines (for example putrescine, spermine, spermidine), structural ACC analogs (for example α-aminoisobutyric acid, L-aminocyclopropene-1-carboxylic acid), salicylic acid [C. A. Leslie and R. J. Romani (1988), Inhibition of ethylene bio-synthesis by salicylic acid, Plant Physiology 88: 833-837] including its synthetic analogon acibenzolar-S-methyl, structural analogs of ascorbic acid which act as inhibitors of ACC oxidase [for example prohexadione-Ca, trinexapac-ethyl—W. Rademacher (2000), Growth retardants: Effects on gibberellin biosynthesis and other metabolic pathways, Annual Review of Plant Physiology and Plant Molecular Biology 51: 501-531] and also triazolyl compounds as inhibitors of cytochrome P-450-dependent monooxygenases whose main action is to block the biosynthesisof gibberellins [for example paclobutrazol, uniconanzole—W. Rademacher (2000), Growth retardants: Effects on gibberellin biosynthesis and other metabolic pathways, Annual Review of Plant Physiology and Plant Molecular Biology 51: 501-531].

Inhibitors of the Action of Ethylene

These substances bind, for example, with high affinity to the ethylene receptor in the target tissue, thus blocking the action of ethylene [structural analogs of ethylene (for example 1-methylcyclopropene, 2,5-norbornadiene), 3-amino-1,2,4-triazole or Ag$^{++}$ ions (for example from silver thiosulfate)].

For some of these ethylene modulators, various additional actions are described in the literature. It is mentioned, for example, that acylcyclohexanediones such as prohexadione- Ca or trinexapac-ethyl can provide protection of crop plants against biotic and abiotic stressors [for example EP 0 123 001 A1, page 27, lines 20 and 21 (for prohexadione and related substances) or for trinexapac-ethyl and related compounds in EP 0 126 713]. Bazzi et al. (European Journal of Horticultural Science 68: 108-114 and 115-122) mention a number of examples in which the compounds mentioned induce resistance against specific pathogens in certain host plants. However, in some host/pathogen combinations, no such effect is achieved. There are no examples for legumes.

Cobalt is important as a trace element for plant nutrition. Inhibitors of ethylene biosynthesis which inhibit the conversion of S-adenosyl-L-methionine into ACC are described as also being able to reduce the formation of ethylene in soils used for agriculture. This facilitates improved plant growth and, in the case of legumes, a more intensive root nodulation (EP-A 0 767 607).

Other types of the ethylene modulators mentioned have been examined by different groups for their ability to exert an effect against biotic or abiotic stressors on crop plants. It is known that triazolyl compounds such as paclobutrazol and uniconazole have a certain fungicidal action owing to their structural similarity to certain fungicides [cf. W. Rademacher (2000), Growth retardants: Effects on gibberellin biosynthesis and other metabolic pathways, Annual Review of Plant Physiology and Plant Molecular Biology 51: 501-531]. Salicylic acid and acibenzolar-S-methyl, which is derived therefrom, trigger resistance reactions against infection by pathogens [M. Oostendorp et al. (2001), Induced disease resistance in plants by chemicals, European Journal of Plant Pathology 107:19-28]. However, there are no indications in the relevant literature that the ethylene modulators mentioned act against plant damage caused by fungi specifically in soybeans.

Surprisingly, it has now been found that the simultaneous use of fungicidal compounds of the formula I and, if appropriate, azoles III, and of ethylene modulators II allows better prevention of plant damage caused by pathogens (in particular premature leaf drop) in legumes than treatment with fungicide alone. The direct results are increased yields, combined with a better quality of the harvested material.

Also it has been found that the simultaneous use of fungicidal compounds of formula I and, if appropriate, azoles III, and of ethylene modulators III reduce the ethylene evolution of non-pathogen effected plants.

Fungicides suitable for controlling harmful fungi, in particular *Phakopsora pachyrhizi* and *Phakopsora meibomiae*, are the compounds of the formula I mentioned at the outset (strobilurins).

Azoxystrobin, dimoxystrobin, fluoxastrobin, kresoxim-methyl, metominostrobin, orysastrobin, picoxystrobin and trifloxystrobin and particularly preferably pyraclostrobin have been found to be particularly suitable for controlling the fungal diseases mentioned above.

The strobilurins mentioned above are known from the literature

- dimoxystrobin, (E)-2-(methoxyimino)-N-methyl-2-[α-(2,5-xylyloxy)-otolyl]acetamide, known from EP-A 477 631 and EP-A 398 692;
- azoxystrobin, methyl (E)-2-{2-[6-(2-cyanophenoxy)pyrimidin-4-yloxy]phenyl}-3-methoxyacrylate, known from EP 382375;
- fluoxastrobin, (E)-{2-[6-(2-chlorophenoxy)-5-fluoropyrimidin-4-yloxy]phenyl}(5,6-dihydro-1,4,2-dioxazin-3-yl)methanone O-methyloxime, known from WO 95/04728;
- kresoxim-methyl, methyl (E)-methoxyimino[α-(o-tolyloxy)-o-tolyl]acetate, known from EP 253 213;
- metominostrobin, (E)-2-(methoxyimino)-N-methyl-2-(2-phenoxyphenyl)-acetamide, known from EP-A 398 692;
- orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide, known from WO-A 97/15552;
- picoxystrobin, methyl (E)-3-methoxy-2-{2-[6-(trifluoromethyl)-2-pyridykmmethyl]phenyl}acrylate, known, for example, from EP 278595; pyraclostrobin, methyl N-{2-[1-(4-chlorophenyl)-1H-pyrazol-3-yloxymethyl] phenyl}(N-methoxy)carbamate, known, for example, from EP 804 421;
- trifloxystrobin, methyl (E)-methoxyimino-{(E)-α-[1-(α,α,α-trifluoro-m-tolyl)ethylideneaminooxy]o-tolyl}acetate, known from EP-A 460575.

In addition to their excellent action against rust fungi, the strobilurins also increase the yield capacity of legumes. Legumes include, in particular, the following crop plants: lupins, clover, lucerne, peas, beans (Phaseolus and Vicia species), lentils, chick-peas, peanuts and in particular soybeans. Yield increases not due to the fungicidal action of the strobilurins have already been reported for the use of strobilurins in cereals (Koehle H. et al, in *Gesunde Pflanzen* 49 (1997), pages 267-271; Glaab J. et al. *Planta* 207 (1999), 442-448).

When using strobilurins, in particular pyraclostrobin, in soybeans, the yield increase is surprisingly high. The increase in yield capacity in combination with the excellent action of the strobilurins against rust in legumes makes the method according to the invention particularly interesting for the farmer. Excellent results can be obtained when using pyraclostrobin.

Furthermore, the method according to the invention also allows effective control of other harmful fungi frequently encountered in legumes. The most important fungal diseases in soybeans are listed below:

*Microsphaera diffusa*
*Cercospora kikuchii*
*Cercospora sojina*
*Septoria glycines*
*Colletotrichum truncatum*
*Corynespora cassiicola*

As mentioned at the outset, ethylene modulators are preferably to be understood as meaning the following compounds: rhizobitoxin, aminoethoxyvinylglycine, methoxyvinylglycine, L-canaline, aminooxyacetic acid, oxime ether derivatives (according to EP-A-0 243 834 and EP-A 0 501 326), $Co^{++}$ or $Ni^{++}$ ions, n-propyl gallate, putrescine, spermine, spermidine, α-aminoisobutyric acid, L-aminocyclopropene-1-carboxylic acid, salicylic acid, acibenzolar-S-methyl, prohexadione-Ca, trinexapac-ethyl, paclobutrazol, uniconanzole, 1-methylcyclopropene, 2,5-norbornadiene, 3-amino-1,2,4-triazole or $Ag^{++}$ ions.

Ethylene modulators which are particularly suitable for the mixtures according to the invention are aminoethoxyvinylglycine, aminooxyacetic acid, $Co^{++}$ ions in plant-available form (inorganic salts, complexes or chelates with organic compounds, examples hereof are inter alia $CoCl_2$×6 $H_2O$, PhytoPlus Cobalt [Baicor LC, Logan Utah 84321, USA], Keylate Cobalt [Stoller Enterprises, Houston, Tex. 77043]), α-aminoisobutyric acid, salicylic acid, acibenzolar-S-methyl, prohexadione-Ca and trinexapac-ethyl.

Particular preference is given to $Co^{++}$ ions in plant-available form (inorganic salts, complexes or chelates with organic compounds, like $CoCl_2$×6 $H_2O$, PhytoPlus Cobalt [Baicor LC, Logan Utah 84321, USA], Keylate Cobalt [Stoller Enterprises, Houston, Tex. 77043]), salicylic acid and prohexadione-Ca (EP-A 123001). Here, it is possible to use, according to the invention, one or more of these ethylene modulators in a mixture with strobilurins (if appropriate together with an additional azole).

In general, the strobilurins (I) and the ethylene modulators (II) are employed in a weight ratio of from 20:1 to 0.05:1, preferably in a weight ratio of from 10:1 to 0.05:1 and with particular preference in a weight ratio of from 5:1 to 0.1:1. The weight proportion of the ethylene modulators may be made up of a number of active compounds.

The mixtures of strobilurin with ethylene modulators are suitable for controlling the abovementioned diseases. However, it is possible to add further active compounds to the mixtures, such as, for example, herbicides, insecticides, growth regulators, fungicides or else fertilizers. When the strobilurins or the compositions comprising them in the use form as fungicide are mixed with other fungicides, frequently a broader fungicidal activity spectrum is obtained.

The following list of fungicides, together with which the compounds according to the invention can be used, is intended to illustrate the possible combinations, but not to impose any limitation:

acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph anilinopyrimidines such as pyrimethanil, mepanipyrim or cyprodinyl, antibiotics such as cycloheximide, griseofulvin, kasugamycin, natamycin, polyoxin or streptomycin, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocylic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl phenylpyrroles such as fenpiclonil or fludioxonil, sulfur other fungicides such as benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamide sulfenic acid derivatives such as captafol, captan, dichlofluanid, folpet, tolylfluanid cinnamides and analogs such as dimethomorph, flumetover or flumorph.

Mixtures which, in addition to strobilurins I and ethylene modulators II, contain an azole III, such as, for example, bromoconazole, cyproconazole, epoxiconazole, fenbuconazole, fluquiconazole, flusilazole, metconazole, myclobutanil, propiconazole, prochloraz, prothioconazole, tebuconazole or triticonazole, have been found to be suitable for the process according to the invention. Particular preference is given to the mixture of pyraclostrobin, ethylene modulators II and epoxiconazole.

The mixtures according to the invention are used by treating the fungi or the plants, materials or the soil to be protected against fungal attack with an effective amount of the combinations of active compounds. Especially the above-ground plant parts of the legumes, in particular the leaves, are treated with an aqueous preparation of the active compounds. Application can be carried out either before or after the infection of the materials or plants by the fungi.

The mixtures increase the yield capacity in particular of legumes. They are of particular importance for the treatment of lupins, clover, lucerne, peas, beans (Phaseolus and Vicia species), lentils, chick-peas, peanuts and especially soybeans.

As mentioned further above, certain ethylene modulators reduce the formation of ethylene in the soil, i.e. in the root region of the useful plants (EP-A 767 607). It has to be assumed that even after foliar application a certain proportion of such substances will end up in the soil (for example when being washed off by falling rain). Accordingly, part of the active compound combination according to the invention has an additional useful effect in improving the soil: a reduced ethylene content in the rhizosphere generally allows better plant growth; in the case of legumes, more root nodules are formed, resulting in increased assimilation of $N_2$. These effects may additionally enhance the yield.

A particular embodiment of the process according to the invention relates to the use of the mixtures in genetically modified legumes, in particular soybeans. Soybeans which, for example, are resistant against herbicides such as glyphosate or plants which form insecticidally active compounds are now commercially available. Some of the genetically modified plants are more sensitive than customary breeds. Moreover, the corresponding seed is generally more expensive, so that the protection of these crop plants is particularly important.

Methods for producing plants which are resistant to glyphosate action have been described in the recent literature (EP-A 218 571, EP-A 293 358, WO-A 92/00377 and WO-A 92/04449). Chemical Abstracts, 123, No. 21 (1995) A.N. 281158c describes the production of glyphosate-resistant soybeans. Other glyphosate-resistant legumes can be produced in a similar manner. Methods for transforming legumes are known in the literature and can be used as outlined above to produce, for example, glyphosate-resistant beans, peas, lentils, peanuts and lupins: *Plant Science* (Shannon) 150(1) Jan. 14.2000, 41-49; *J. of Plant Biochemistry & Biotechnology* 9(2) July, 2000, 107-110; *Acta Physiologiae Plantarum* 22(2), 2000, 111-119; *Molecular Breeding* 5(1) 1999, 43-51; *In Vitro Cellular & Developmental Biology, Animal* 34 (3 Part 2) March, 1998, 53A; *Plant Cell Reports* 16(8), 1997, 513-519 and 541-544; *Theoretical & Applied Genetics* 94(2), 1997, 151-158; *Plant Science*, 117 (1-2), 1996, 131-138; *Plant Cell Reports* 16(1-2), 1996, 32-37.

It is possible to use, for example, soybean cultivars such as NIDERA AX 4919 which are resistant against numerous fungal diseases and the herbicide glyphosate.

When using the active compound mixtures according to the invention in crop protection, the application rates are from 0.05 to 2.0 kg of active compound per ha, depending on the nature of the desired effect.

If mixtures of strobilurins (I) and azoles (III) are used in mixing component a), the weight ratio of the compounds I to III is usually from 20:1 to 0.05:1 and preferably from 10:1 to 0.1:1.

In the case of mixtures according to the invention of fungicides (I+III) and ethylene modulators (II), the weight ratio is from 20:1 to 0.05:1, preferably from 10:1 to 0.1:1. Here, a plurality of ethylene modulators (II) may be present together.

The mixtures can be converted into the customary formulations, for example solutions, emulsions, suspensions, dusts, powders, pastes and granules. The use form depends on the particular purpose; in any case, it should ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates (for example sodium dodecyl sulfate), alkylsulfonates, fatty alcohols (for example Lutensol® AO 10), fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octyl phenyl ether, ethoxylated isooctylphenol, octylphenol, nonylphenol, alkylphenyl polyglycol ether (for example Triton® X-100), tributylphenyl polyglycol ether, tristerylphenyl polyglycol ether, alkylaryl polyether alcohols, alcohol and fatty alcohol/ethylene oxide condensates, fatty alcohol alkoxylates (for example Wettol® LF700), ethoxylated castor oil, polyoxyethylene alkyl ethers, ethoxylated polyoxypropylene, lauryl alcohol polyglycol ether acetal, sorbitol esters, polyoxyethylene sorbitan monolaurate (for example Tween® 20), lignosulfite waste liquors and methylcellulose.

In a preferred embodiment, mixtures according to the invention comprising strobilurins I, ethylene modulators II, if appropriate azoles III and surfactants selected from the group consisting of alkyl sulfates (for example sodium dodecyl sulfate), fatty alcohols (for example Lutensol® AO 10), polyoxyethylene sorbitan monolaurate (for example Tween® 20), alkylphenyl polyglycol ethers (for example Triton® X-100), fatty alcohol alkoxylates (for example Wettol® LF700) are used.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone or water.

Powders, materials for spreading and dusts can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths, such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, for example ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of "the active ingredient". ("The active ingredients" means in this context a compound of the formula I, one or more ethylene modulators (II) and, if desired, one or more further active compound, like a herbicide, insecticide, another fungicide etc.) The compounds of formula I, the ethylene modulators and, if desired, the further active compounds are in this case employed in a purity of from 90% to 100%, preferably 95% to 100% (according to NMR spectrum).

The following are exemplary formulations:

1. Products for Dilution with Water

A) Water-Soluble Concentrates (SL)

10 parts by weight of "the active ingredients" according to the invention are dissolved in water or in a water-soluble solvent. As an alternative, wetters or other auxiliaries are added. The active compound dissolves upon dilution with water.

B) Dispersible Concentrates (DC)

20 parts by weight of "the active ingredients" according to the invention are dissolved in cyclohexanone with addition of dispersant, for example polyvinylpyrrolidone. Dilution with water gives a dispersion.

C) Emulsifiable Concentrates (EC)

15 parts by weight of "the active ingredients" according to the invention are dissolved in xylene with addition of calcium dodecylbenzenesulfonate and castor oil ethoxylate (in each case 5% strength). Dilution with water gives an emulsion.

D) Emulsions (EW, EO)

40 parts by weight of "the active ingredients" according to the invention are dissolved in xylene with addition of calcium dodecylbenzenesulfonate and castor oil ethoxylate (in each case 5% strength). This mixture is introduced into water by means of an emulsifier (Ultraturrax) and made into a homogeneous emulsion. Dilution with water gives an emulsion.

E) Suspensions (SC, OD)

In an agitated ball mill, 20 parts by weight of "the active ingredients" according to the invention are comminuted with addition of dispersants, wetters and water or an organic solvent to give a fine active compound suspension. Dilution with water gives a stable suspension of the active compound.

F) Water-Dispersible Granules and Water-Soluble Granules (WG, SG)

50 parts by weight of "the active ingredients" according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-Dispersible Powders and Water-Soluble Powders (WP, SP)

75 parts by weight of "the active ingredients" according to the invention are ground in a rotor-stator mill with addition of dispersants, wetters and silica gel. Dilution with water gives a stable dispersion or solution of the active compound.

2. Products to be Applied Undiluted

H) Dustable Powders (DP)

5 parts by weight of "the active ingredients" according to the invention are ground finely and mixed intimately with 95% of finely divided kaolin. This gives a dustable product.

I) Granules (GR, FG, GG, MG)

0.5 part by weight of "the active ingredients" according to the invention is ground finely and associated with 95.5% carriers. Customary methods are extrusion, spray-drying or the fluidized bed. This gives granules to be applied undiluted.

J) ULV Solutions (UL)

10 parts by weight of "the active ingredients" according to the invention are dissolved in an organic solvent, for example xylene. This gives a product to be applied undiluted.

"The active ingredients" can be used as such, in the form of their formulations or the use forms prepared therefrom, for example in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they are intended to ensure the finest possible distribution of the active compounds according to the invention.

Aqueous use forms can be prepared from emulsion concentrates, pastes or wettable powders (wettable powders, oil dispersions) by adding water. To prepare emulsions, pastes or oil dispersions, the substances as such or dissolved in an oil or solvent can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

"The active ingredients" concentrations in the ready-to-use preparations can be varied within substantial ranges. In general, they are from 0.0001 to 10%, preferably from 0.01 to 1%.

"The active ingredients" may also be used successfully in the ultra-low-volume process (ULV), it being possible to apply formulations comprising over 95% by weight of "active ingredients", or even "the active ingredients" without additives.

Various types of oils, wetting agents, adjuvants, herbicides, fungicides, other pesticides, or bactericides may be added to the active compounds, if appropriate also just prior to use (tank mix). These agents can be admixed with the agents according to the invention in a weight ratio of 1:10 to 10:1.

It has also been found that $Co^{++}$ ions in plant-available form (inorganic salts, complexes or chelates with organic compounds, examples hereof are inter alia $CoCl_2 \times 6 \; H_2O$, PhytoPlus Cobalt [Baicor LC, Logan Utah 84321, USA], Keylate Cobalt [Stoller Enterprises, Houston, Tex. 77043]) are useful to control harmful fungi.

Usually these $Co^{++}$ ions in plant-available form are applied at an application rate of 10 to 100 g/ha (based on $Co^{++}$).

The $Co^{++}$ ions in plant-available form may also be mixed together or applied together with further active compounds, such as, for example, herbicides, insecticides, growth regulators, other fungicides or fertilizers. When the $Co^{++}$ ions in plant-available form or the compositions comprising them in the use form as fungicide are mixed with other fungicides, frequently a broader fungicidal activity spectrum is obtained. The additional fungicides are, such as, for example, strobilurins as mentioned before and/or acylalanines, amine derivatives, anilinopyrimidines, antibiotics, dicarboximides, dithiocarbamates, heterocyclic compounds, copper fungicides, nitrophenyl derivatives, phenylpyrroles, sulphur, other fungicides, sulfenic acid derivatives cinnamides and analogs as mentioned before.

The $Co^{++}$ ions in plant-available form can be converted into the customary formulations similar to those of the mixtures as mentioned before. These are prepared in a known manner also similar to the preparation of the mixtures as mentioned before.

The $Co^{++}$ ions in plant-available form according to the invention are used by treating the fungi or the plants, materials or the soil to be protected against fungal attack with an effective amount of the combinations of active compounds. Especially the above-ground plant parts of the legumes, in particular the leaves, are treated with an aqueous preparation of the active compounds. Application can be carried out either before or after the infection of the materials or plants by the fungi.

USE EXAMPLE

Example 1

During fruit formation, soybeans of the cultivar RS10 with 8-12% preinfection by *Phakopsora pachyrhizi* were treated by spray application using customary sprayers with a mixture of 133 g/ha of pyraclostrobin, 80 g/ha of $CoCl_2 \times 6 \; H_2O$ (=20 g/ha of cobalt) and 100 g/ha of prohexadione-Ca. Entirely untreated plants and plants treated with 133 g/ha of pyraclostrobin were used for comparison. 8 days after the treatment, the plants which had been treated with the pure fungicide variant showed less infection by pathogen than the entirely untreated plants. However, here, too, there was considerable leaf drop. This leaf drop was considerably less pronounced when the treatment was carried out using the mixtures according to the invention. Furthermore, compared with the pure fungicide mixture and even more so compared with the entirely untreated plants the mixture according to the invention gave a significant additional yield of soybeans.

Example 2

Soybean plants were raised under greenhouse conditions with two plants each per 12-cm pot. Spray treatments of the leaves were carried out with a volume of liquid of 750 l/ha when the plants had developed one to two trifoliate leaves. 24 hours after treatment, the shoots of the soybean plants were dissected above the cotyledons and wilted for 10 minutes under laboratory conditions. Shoots representing a distinct treatment were incubated for 60 minutes under laboratory conditions in a 100-ml Erlenmeyer flask sealed with a rubber cap. Thereafter, gas samples were taken and analyzed for their ethylene content by gas chromatography.

| Reduction of ethylene formation in leaves of soybean plants (cv. "Delta Pine") | | | | |
|---|---|---|---|---|
| No. | Product Name | Active Ingredient (ai) | Dosage [g/ha of ai] | Ethylene Evolution per Unit Leaf Weight [% of Control] |
| 1 | Control | — | 0 | 100 |
| 2 | $CoCl_2 \times 6H_2O$ | $Co^{++}$ | 40 | 41 |
| 3 | Cabrio[(a)] | Pyraclostrobin | 100 | 87 |
| 4 | Salicylic Acid | Salicylic Acid | 500 | 97 |
| 5 | Cabrio[(a)] + $CoCl_2 \times 6H_2O$ | Pyraclostrobin + $Co^{++}$ | 100 + 40 | 34 |
| 6 | Cabrio[(a)] + Salicylic Acid | Pyraclostrobin + Salicylic Acid | 100 + 500 | 74 |

[(a)]Producer, Holder of Trade Name: BASF AG, Germany

The results obtained indicate that the fungicide pyraclostrobin inhibits ethylene formation in drought-stressed soybean leaves. Similar effects are obtained with several ethylene modulators. Combinations of pyraclostrobin with ethylene modulators give additive effects.

Example 3

Seeds of soybean cv. "Embrapa 48" were planted and grown under standard conditions with adequate supply of water and nutrients. Infection with *Phakopsora pachyrhizi* occurred naturally. The active ingredients have been applied twice, 62 and 68 days after seeding. The dosages used and the obtained results are shown below.

| Yield improvement of soybeans (cv. "Embrapa 48) | | | | |
|---|---|---|---|---|
| No. | Product Name | Active Ingredient (ai) | Dosage [g/ha of active ingredient] | Seed Yield [kg/ha] |
| 1 | Control | — | — | 1439 |
| 2 | Headline[(a)] | Pyraclostrobin | 112.5 | 1782 |
| 3 | Keylate Cobalt[(b)] | $Co^{++}$ | 29 | 1760 |
| 4 | Headline[(a)] + Keylate Cobalt[(b)] | Pyraclostrobin + $Co^{++}$ | 112.5 + 29 | 2490 |

[(a)]Producer, Holder of Trade Name: BASF AG, Germany
[(b)]Producer, Holder of Trade Name: Stoller Enterprise, Houston TX 77043, USA The results obtained demonstrate that the fungicide pyraclostrobin as well as the ethylene modulator $Co^{++}$ increase the seed yield. This yield is increased significantly when combinations of the fungicide with the ethylene modulator is used. The seed yield amounts 73% above the control compared to a seed yield improvement of 24% and 22%, respectively, in case pyraclostrobin and $Co^{++}$ are applied alone.

Example 4

Soybeans cv. "Embrapa 48" have been planted and grown under standard conditions and have been infected with *Phakopsora pachyrhizi*. 62 and 68 days after seeding the soybeans have been treated with 29 g/ha $Co^{++}$ (Keylate Cobalt with 5% Cobalt [Producer, Holder of Trade Name: Stoller Enterprise, Houston Tex. 77043, USA]). 8 days later the treated soybeans showed a damage of 7.9% whereas the damage of the control plants has been 13%.

The invention claimed is:

1. A mixture, comprising pyraclostrobin and prohexadione-Ca in a weight ratio of from 20:1 to 0.05:1.

2. The mixture as claimed in claim 1, further comprising $Co^{++}$ ions.

3. The mixture as claimed in claim 1 which additionally comprises an azole III selected from the group consisting of bromoconazole, cyproconazole, epoxiconazole, fenbuconazole, fluquiconazole, flusilazole, metconazole, myclobutanil, propiconazole, prochloraz, prothioconazole, tebuconazole and triticonazole.

4. The mixture as claimed in claim 1 which additionally comprises a surfactant selected from the group consisting of: polyoxyethylene sorbitan monolaurate, alkylphenoxy polyethoxy ethanol, fatty alcohol, fatty alcohol alkoxylate and sodium dodecylsulfate.

5. A method for controlling rust infections in legumes, which comprises treating the above-ground plant parts of the legumes with an aqueous preparation of a mixture as claimed in claim 1.

6. The method as claimed in claim 5, wherein rust infection on leaves and fruits of soya plants is controlled.

7. The method as claimed in claim 5, wherein the rust infection is caused by *Phakopsora pachyrhizi* and/or *Phakopsora meibomiae*.

8. A method for increasing the yield and quality of legumes which comprises applying an effective amount of a mixture as claimed in claim 1.

9. A method for reducing the ethylene evolution of plants by which comprises applying an effective amount of a mixture as claimed in claim 1.

10. A method for reducing undesired defoliation of crop plants which comprises applying an effective amount of a mixture as claimed in claim 1.

* * * * *